United States Patent
Hu et al.

(10) Patent No.: US 12,075,848 B2
(45) Date of Patent: Sep. 3, 2024

(54) GAS ADJUSTING ASSEMBLY, GAS ADJUSTING BELT, BATTERY DEVICE AND ELECTRONIC ATOMIZATION EQUIPMENT

(71) Applicant: Shenzhen Smoore Technology Limited, Shenzhen (CN)

(72) Inventors: Weiguang Hu, Shenzhen (CN); Yongcheng Zhou, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 474 days.

(21) Appl. No.: 17/365,872

(22) Filed: Jul. 1, 2021

(65) Prior Publication Data

US 2022/0061400 A1     Mar. 3, 2022

(30) Foreign Application Priority Data

Sep. 1, 2020    (CN) .................. 202021898516.X

(51) Int. Cl.
    *A24F 40/50*        (2020.01)
    *A24F 40/10*        (2020.01)
    (Continued)

(52) U.S. Cl.
    CPC .............. *A24F 40/95* (2020.01); *A24F 40/10* (2020.01); *A24F 40/42* (2020.01); *A24F 40/50* (2020.01)

(58) Field of Classification Search
    CPC ................................ A24F 40/50; A24F 40/95
    See application file for complete search history.

(56) References Cited

U.S. PATENT DOCUMENTS

| | | | | |
|---|---|---|---|---|
| 4,553,663 A | * | 11/1985 | Johnson ................. | A01D 61/02 198/848 |
| 2012/0103764 A1 | * | 5/2012 | Price ...................... | B65G 15/30 198/844.2 |

(Continued)

FOREIGN PATENT DOCUMENTS

| CN | 111165893 A | 5/2020 |
|---|---|---|
| CN | 210747256 U | 6/2020 |

(Continued)

OTHER PUBLICATIONS

Liu et al., Battery Assembly and Electronic Cigarette (English machine translation), 2023, Clarivate Analytics, WO 2017075753 A1, 1-14 (Year: 2023).*

(Continued)

*Primary Examiner* — Philip Y Louie
*Assistant Examiner* — Jeffrey A. Buckman

(57) ABSTRACT

The present disclosure discloses a gas adjusting assembly, a gas adjusting belt, and an electronic atomization equipment. The gas adjusting assembly includes: a bracket provided with a first gas inlet; a gas adjusting belt comprising a flexible belt body and a second gas inlet disposed on the flexible belt body, two ends of the flexible belt body are connected to each other, and the flexible belt body surrounds a periphery of the bracket, the second gas inlet and the first gas inlet are set in one-to-one correspondence; the flexible belt body is configured to slide relative to the bracket. Since the flexible belt body is foldable, and it surrounds the periphery of the bracket, thus the gas adjusting assembly provided by the present disclosure has no specific requirements on the shape and structure of the bracket and the gas adjusting belt is easy to install.

15 Claims, 4 Drawing Sheets

(51) Int. Cl.
  *A24F 40/42* (2020.01)
  *A24F 40/95* (2020.01)

(56) References Cited

U.S. PATENT DOCUMENTS

2019/0364966 A1* 12/2019 Liu .......................... A24F 7/02
2020/0173522 A1*  6/2020 Godsey ................... F16G 1/28

FOREIGN PATENT DOCUMENTS

WO   WO-2016201602 A1 * 12/2016   ............. A24F 47/00
WO   WO-2017075753 A1 *  5/2017   ............. A24F 47/00

OTHER PUBLICATIONS

Liu et al., Electronic Cigarette (English machine translation), 2023, Clarivate Analytics, WO 2016201602 A1, 1-16 (Year: 2023).*
European search report, European Application No. 21186605.8, mailed Jan. 20, 2022 (10 pages).

* cited by examiner

GAS ADJUSTING ASSEMBLY, GAS ADJUSTING BELT, BATTERY DEVICE AND ELECTRONIC ATOMIZATION EQUIPMENT

CROSS REFERENCE

The present application claims the priority of Chinese Patent Application No. 202021898516.X, filed on Sep. 1, 2020, which is entirely incorporated into the present application by reference.

TECHNICAL FIELD

The present disclosure relates to the field of atomization technology, and in particular, to a gas adjusting assembly, a gas adjusting belt, a battery device, and an electronic atomization equipment.

BACKGROUND

The existing electronic atomization equipment is mainly composed of an atomizer and battery device. The atomizer atomizes an atomizable matrix. The battery device is used to power the atomizer. The lung capacity of each user is different. Each user needs to match an appropriate gas intake when using the electronic atomization equipment, so that the user can experience a better suction feeling.

However, in the existing electronic atomization equipment, a gas adjusting ring is usually used for gas adjustment. The gas adjusting ring has specific requirements for the shape and structure of the electronic atomization equipment, and its installation structure in the electronic atomization equipment is also relatively complex.

SUMMARY

In some aspects of the present disclosure, a gas adjusting belt for an electronic atomization equipment may be provided. A gas adjusting assembly includes a bracket provided with a first gas inlet and a gas adjusting belt. The gas adjusting belt includes a flexible belt body and a second gas inlet. The flexible belt body surrounds a periphery of the bracket, a first surface of the flexible belt body is provided with a plurality of protrusions, each of the plurality of protrusions includes a surface away from the flexible belt body, and the surface of each of the plurality of protrusions abuts against a peripheral wall of the bracket. The second gas inlet is disposed through the flexible belt body, the second gas inlet and the first gas inlet are set in a one-to-one correspondence, and the flexible belt body is configured to slide relative to the bracket.

In some aspects of the present disclosure, a gas adjusting belt is provided. The gas adjusting belt includes a flexible belt body and a second gas inlet. The flexible belt body surrounds a periphery of a bracket, a first surface of the flexible belt body is provided with a plurality of protrusions, each of the plurality of protrusions includes a surface away from the flexible belt body, and the surface of each of the plurality of protrusions abuts against a peripheral of the bracket. The second gas inlet is disposed through the flexible belt body, the second gas inlet is configured to be in one-to-one correspondence with the first gas inlet of the bracket, and the flexible belt body is configured to slide relative to the bracket.

In some aspects of the present disclosure, a gas adjusting belt is provided. The gas adjusting belt includes a flexible belt body and a second gas inlet. The flexible belt body surrounds a periphery of a bracket, a first surface of the flexible belt body is provided with a plurality of protrusions, each of the plurality of protrusions includes a surface away from the flexible belt body, the surface of each of the plurality of protrusions abuts against a peripheral wall of the bracket, and the first surface is close to the peripheral wall of the bracket. The plurality of protrusions include two rows of protrusions, each of two long sides of the first surface of the flexible belt body is provided with a row of protrusions, the first surface of the flexible belt body is provided with a plurality of grooves that are parallel to each other and spaced apart from each other, each of the plurality of grooves extends along a width direction of the flexible belt body. Each of the plurality of grooves is disposed between one protrusion of one row of protrusions and one corresponding protrusion of the other row of protrusions along the width direction of the flexible belt body. The second gas inlet is disposed through the flexible belt body, the second gas inlet is configured to be in one-to-one correspondence with the first gas inlet of the bracket, and the flexible belt body is configured to slide relative to the bracket.

By adjusting the position of gas adjusting belt relative to the bracket, a size of an overlapping area between the second gas inlet and the first gas inlet is adjusted, thereby adjusting the gas intake area of the gas adjusting assembly to obtain different suction feelings. Since the flexible belt body of the gas adjusting belt is foldable, and it surrounds the periphery of the bracket, relatively speaking, an installation of the gas adjusting belt has no specific requirements for the shape and structure of the bracket, just surround the bracket by the flexible belt body. Therefore, the gas adjusting assembly provided in the present disclosure has no specific requirements on the shape and structure of the bracket, and the gas adjusting belt is easy to install.

BRIEF DESCRIPTION OF THE DRAWINGS

In order to illustrate the technical solutions in the embodiments of the present disclosure or the prior art more clearly, the following will briefly introduce the figures needed to be used in the description of the embodiments or the prior art. Obviously, the drawings in the following description are only some embodiments of the present disclosure; those skilled in the art may derive other figures from these figures without paying any creative work.

DETAILED DESCRIPTION

The technical solutions in the embodiments of the present disclosure will be described clearly and completely with reference to the figures in the embodiments of the present disclosure. Obviously, the described embodiments are only a part of the embodiments of the present disclosure, rather than all the embodiments. Based on the embodiments of the present disclosure, all other embodiments obtained by those skilled in the art without any creative work are within the scope of the present disclosure.

The terms "first", "second", and "third" in the embodiments of the present disclosure are only used for descriptive purposes, and cannot be understood as indicating or implying relative importance or implicitly indicating the number of indicated technical features. Thus, the features defined with "first", "second", and "third" may explicitly or implicitly include at least one of the features. In the description of the present disclosure, "a plurality of" means at least two, such as two, three, etc., unless specifically defined otherwise. In addition, the terms "including" and "having" and any variations thereof are intended to cover non-exclusive inclusions. For example, a process, method, system, product, or device that includes a series of steps or units is not limited to the listed steps or units, but optionally includes unlisted steps or units, or optionally also includes other steps or units inherent to these processes, methods, products or equipment.

Mentioning "embodiments" herein means that a specific feature, structure, or characteristic described in conjunction with the embodiments may be included in at least one embodiment of the present disclosure. The appearances of the phrase in various places in the specification are not necessarily all referring to the same embodiment, nor are separate or alternative embodiments mutually exclusive of other embodiments. It is explicitly and implicitly understood by those skilled in the art that the embodiments described herein may be combined with other embodiments.

Figure 1:
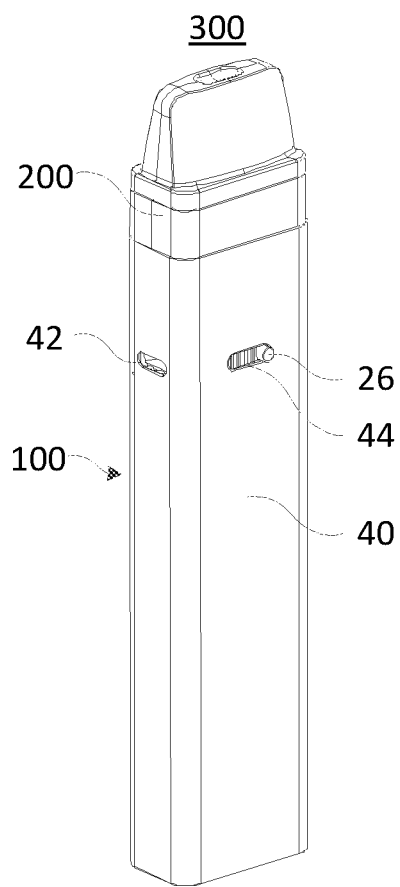
FIG. 1 is a structural schematic view of an embodiment of the electronic atomization equipment provided by the present disclosure.
Figure 2:
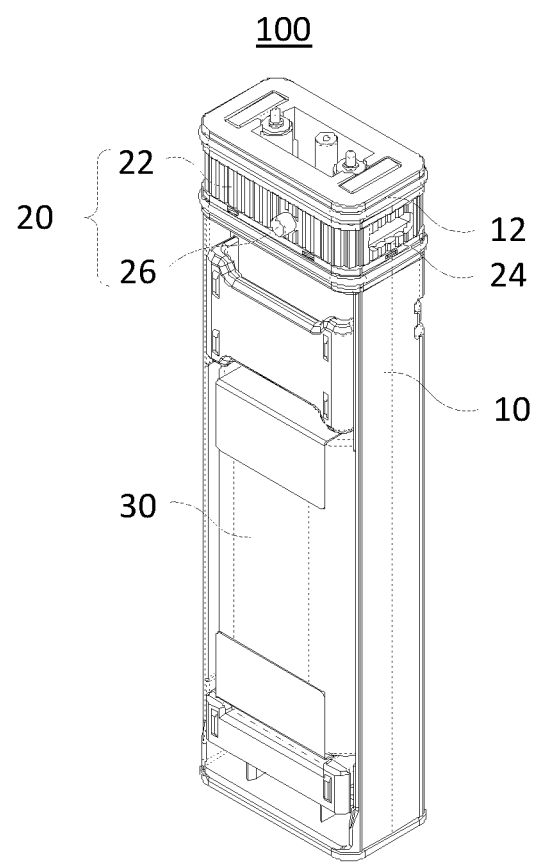
FIG. 2 is a structural schematic view of a battery device of the electronic atomization equipment shown in FIG. 1.
Figure 3:
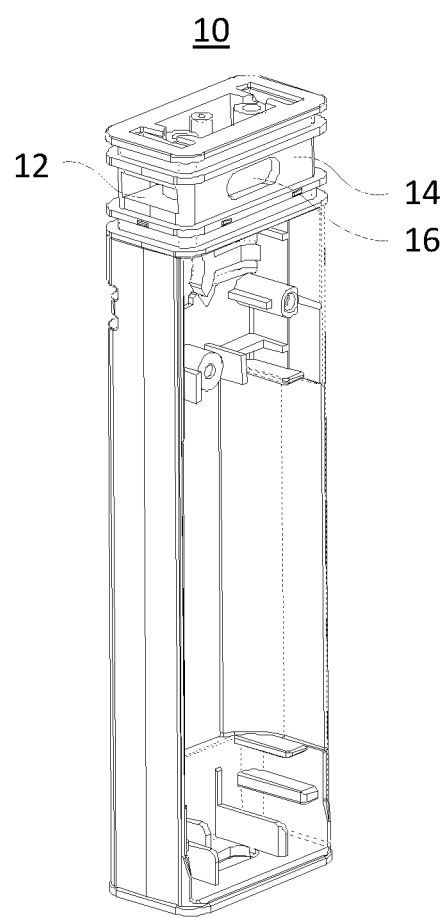
FIG. 3 is a structural schematic view of a bracket of the battery device shown in FIG. 2.
Figure 4:
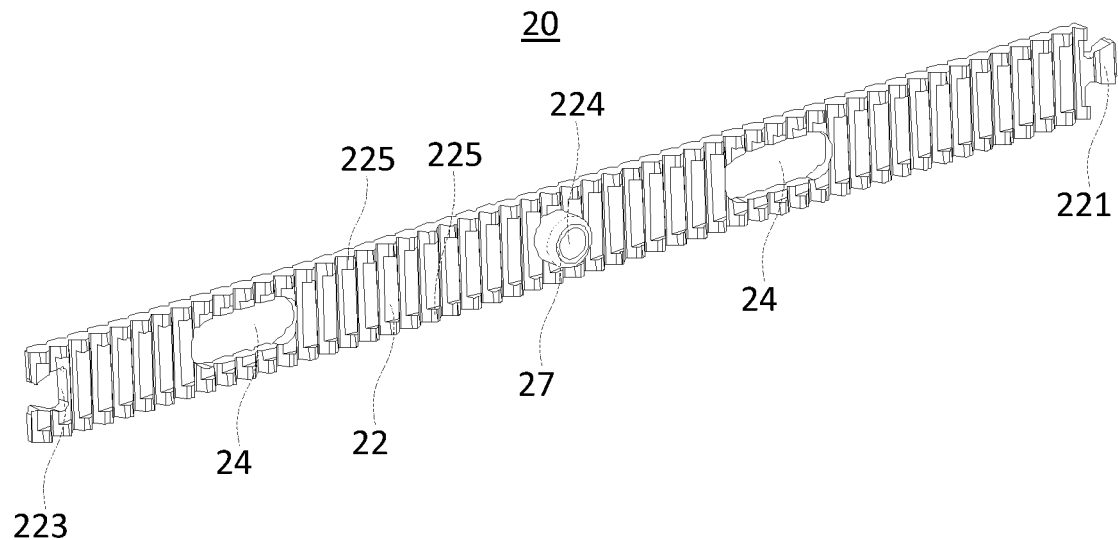
FIG. 4 is a structural schematic view of a gas adjusting belt of the battery device shown in FIG. 2, which is in an extended state.
Figure 5:
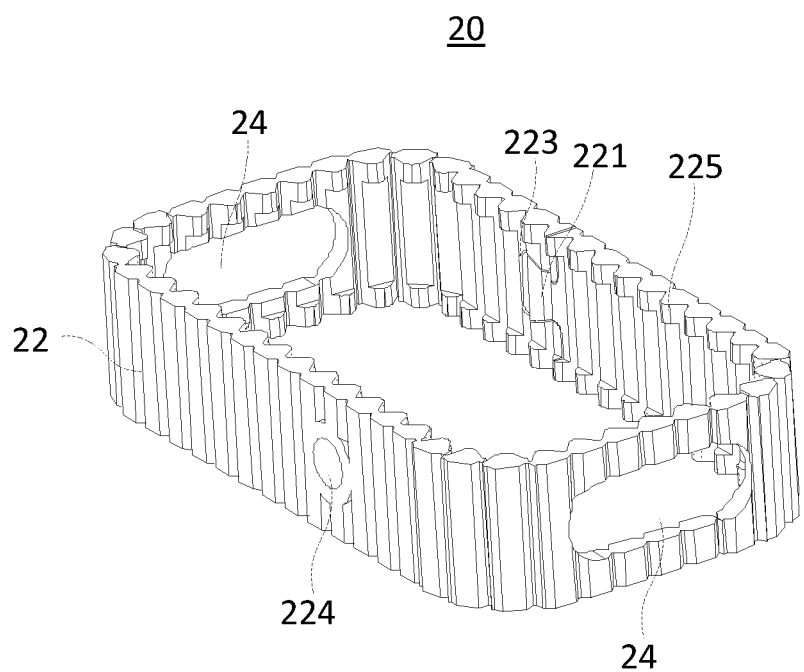
FIG. 5 is a structural schematic view of the gas adjusting belt shown in FIG. 4, which is in an enclosed state.

The present disclosure provides an electronic atomization equipment 300. FIG. 1 is a structural schematic view of an embodiment of the electronic atomization equipment provided by the present disclosure. FIG. 2 is a structural schematic view of a battery device of the electronic atomization equipment shown in FIG. 1, FIG. 3 is a structural schematic view of a bracket of the battery device shown in FIG. 2. FIG. 4 is a structural schematic view of a gas adjusting belt of the battery device shown in FIG. 2, which is in an extended state. FIG. 5 is a structural schematic view of the gas adjusting belt shown in FIG. 4, which is in an enclosed state.

The electronic atomization equipment 300 can be used for the atomization of tobacco oil. As shown in FIG. 1, the electronic atomization equipment 300 comprises an atomizer 200 and a battery device 100. The battery device 100 and the atomizer 200 are interconnected. The atomizer 200 is used to store and atomize a liquid, to form smoke for the user to inhale. The liquid may be a liquid matrix, such as tobacco oil, liquid medicine, and so on. The battery device 100 is used to power the atomizer 200, so that the atomizer 200 can atomize the tobacco oil to form smoke.

Referring to FIGS. 1-3, the battery device 100 comprises a bracket 10, a gas adjusting belt 20, a battery 30, and a housing 40. The battery 30 is disposed on the bracket 10. The bracket 10 and the battery 30 are disposed within the housing 40. The gas adjusting belt 20 is disposed between the housing 40 and the bracket 10. The gas intake area of the battery device 100 is changed by adjusting the gas adjusting belt 20, thereby controlling the gas intake rate and gas intake resistance of the atomizer 200.

The bracket 10 is provided with at least one first gas inlet 12. The atomizer 200 is inserted into the housing 40 and connected to the bracket 10, and an atomizing chamber of the atomizer 200 communicates with the first gas inlet 12. The bracket 10 can be cylindrical, square, flat, or elliptical, etc. The first gas inlet 12 communicate with an end of the bracket 10 towards the atomizer 200. Thus, when the atomizer 200 is connected to the bracket 10, the atomizing chamber of the atomizer 200 communicates with the end of the bracket 10 through a gas hole, such that the first gas inlet 12 communicates with the atomizing chamber of the atomizer 200.

Referring to FIGS. 2-5, the gas adjusting belt 20 comprises a flexible belt body 22 and at least one second gas inlet 24 provided on the flexible belt body 22. Two ends of the flexible belt body 22 are connected to each other and the flexible belt body 22 surrounds a periphery of the bracket 10. The second gas inlet 24 and the first gas inlet 12 are set in a one-to-one correspondence, that is, the projection of second gas inlet 12 on the bracket 10 is overlapped with the first gas inlet partially or totally. A position of the gas adjusting belt 20 relative to the bracket 10 is adjusted along a circumferential direction of the bracket 10, to adjust a size of an overlapping area between the second gas inlet 24 and the first gas inlet 12, thereby changing the gas intake area of the battery device 100.

In some embodiments, the position of the gas adjusting belt 20 relative to the bracket 10 can also be adjusted along an axial direction of the bracket 10, to adjust the size of the overlapping area between the second gas inlet 24 and the first gas inlet 12, thereby changing the gas intake area of the battery device 100.

The shape of the flexible belt body 22 is not limited and can be selected as required. In this embodiment, the flexible belt body 22 is rectangular. The flexible belt body 22 may be a belt body, the whole of which is flexible, such as a pp (polypropylene) material belt, or part of the belt body on the flexible belt body 22 is flexible, and part of the belt body is inflexible. The flexible part of the belt body can be used for bending to fit the bracket 10 of various shapes.

In this embodiment, the two ends of the flexible belt body 22 are connected in a detachable manner. One end of the flexible belt body 22 is provided with a securing tooth 221, the other end of the flexible belt body 22 is provided with a securing mouth 223, and the securing tooth 221 and the securing mouth 223 are connected to each other, so that the flexible belt body 22 can be quickly and detachably connected. Thus, the installation process of the gas adjusting belt 20 is simplified. For example, the securing tooth 221 can be a dovetail tooth, the securing mouth 223 can be a dovetail mouth, and the dovetail teeth and dovetail mouth are connected to form a dovetail buckle. It can be understood that the securing tooth 221 and the securing mouth 223 can also be changed to other securing tooth and securing mouth structures that can realize a connection. Alternatively, the two ends of the flexible belt body 22 can also be connected by a fastener, for example, a pin is used to connect the two ends of the flexible belt body 22. Further, the two ends of the flexible belt body 22 are provided with a plurality of holes, and the different holes at the two ends of the flexible belt body 22 can be connected by a fastener, to adjust the length of the flexible belt body 22 surrounding the periphery of the bracket 10 adaptively.

In other embodiments, the two ends of the flexible belt body 22 can also be connected in an integral structure. Thus, the flexible belt body 22 forms a ring shape, and the flexible belt body 22 is elastic, so that the flexible belt body 22 can be conveniently sleeved on the bracket 10 of various shapes. Further, the bracket 10 can be cylindrical, and the flexible belt body 22 can be sleeved on the bracket 10 more conveniently.

The flexible belt body 22 comprises a first surface and a second surface which are opposite to each other. The first surface of the flexible belt body 22 is provided with a plurality of protrusions 225, the protrusions 225 are configured to abut against a peripheral wall of the bracket 10 to reduce the contact area between the flexible belt body 22 and the bracket 10, thereby reducing the friction between the gas adjusting belt 20 and the bracket 10, so as to adjust the position of the gas adjusting belt 20 relative to the bracket 10 along the circumferential direction of the bracket 10. Therefore, the sensitivity of adjusting the size of the overlapping area between the second gas inlet 24 and the first gas inlet 12 is higher.

In this embodiment, the first surface of the flexible belt body 22 is provided with two rows of protrusions 225 along the extending direction of the flexible belt body 22, and each row of protrusions 225 comprises a plurality of protrusions 225, so that the gas adjusting belt 20 abuts against the peripheral wall of the bracket 10. Specifically, each of two long sides of the first surface comprises a row of protrusions 225, the two long sides of the first surface are parallel to each other and spaced apart from each other. The plurality of protrusions 225 in the same row are evenly spaced apart from each other. The surfaces of the protrusions 225 used to abut against the bracket 10 are circular surfaces, so as to further reduce the friction between the gas adjusting belt 20 and the bracket 10.

In another embodiment, each of the first surface and the second surface is provided with two rows of protrusions 225 to abut against the bracket 10 and the housing 40 respectively. Each of the two long sides on the same surface comprises a row of protrusions 225, the two long sides of the same surface are parallel to each other and spaced apart from each other.

The first surface of the flexible belt body 22 is also provided with a plurality of grooves parallel to each other and spaced apart from each other. The grooves extend along the width direction of the flexible belt body 22, and each end of the each groove is located between two adjacent protrusions 225 of the same row. The grooves are through grooves along the width direction of the flexible belt body 22, thereby reducing the thickness of a portion of the flexible belt body 22, so that the flexible belt body 22 is easier to bend.

In some embodiments, both the first surface and the second surface are provided with a plurality of grooves parallel to each other and spaced apart from each other. In some embodiments, only the second surface is provided with a plurality of grooves parallel to each other and spaced apart from each other.

As shown in FIG. 3, the peripheral wall of the bracket 10 is provided with an annular groove 14, and the gas adjusting belt 20 is disposed within the annular groove 14, so as to facilitate the alignment of the bracket 10 and the gas adjusting belt 20. The first gas inlet 12 is provided on a bottom wall of the annular groove 14, the annular groove 14 limits the position of the gas adjusting belt 20, to improve the alignment accuracy of the second gas inlet 24 and the first gas inlet 12, thereby improving the adjustable range of the overlapping area of the second gas inlet 24 and the first gas inlet 12, so that the gas intake area of the battery device 100 has a wider upper and lower adjustment limits. In this embodiment, the peripheral wall of the bracket 10 is a rectangular peripheral wall, and is provided with two first gas inlets 12 parallel to each other and spaced apart from each other. The first gas inlets 12 are located on the bottom wall of the annular groove 14.

As shown in FIGS. 2, 4, and 5, the flexible belt body 22 is also provided with a connecting hole 224, the connecting hole 224 is connected with a gas adjusting toggle 26, and the position of the gas adjusting belt relative to the bracket is adjusted by dialing the gas adjusting toggle 26. The gas adjusting toggle 26 may be a fastener such as a bolt or a screw.

In another embodiment, the gas adjusting toggle 26 is a convex column integrally connected to the side of the flexible belt body 22 away from the bracket 10, and the position of the gas adjusting belt 20 is adjusted along a circumferential direction by dialing the convex column.

Furthermore, referring to FIGS. 3 and 4, the gas adjusting belt 20 further comprises a limiting column 27 connected to the flexible belt body 22, the peripheral wall of the bracket 10 is also provided with a limiting groove 16, and the limiting column 27 is received in the limiting groove 16. The limiting groove 16 limits the limiting column 27 along a circumferential direction, to limit the adjustment range of the gas adjusting belt 20 along the bracket 10. When the limiting column 27 is located at one end of the limiting groove 16, the second gas inlet 24 totally overlaps the first gas inlet 12, so that the battery device 100 has a largest gas intake area. When the limiting column 27 is located in the other end of the limiting groove 16, the second gas inlet 24 and the first gas inlet 12 are totally misaligned, so that the flexible belt body 22 blocks the first gas inlet 12, and the gas intake area of the battery device 100 is zero.

In this embodiment, one end of the gas adjusting toggle 26 is disposed within the connection hole 224. The connection hole 224 further extends into the limiting column 27 to deepen the depth of the connection hole 224, so that the connection of the gas adjusting toggle 26 and the flexible belt body 22 is more stable. That is, an end of the gas adjusting toggle 26 is disposed within a portion of the connection hole 224 defined by the limiting column 27.

In some embodiments, the connection hole 224 further extends through the limiting column 27 to deepen the depth of the connection hole 224.

Referring to FIG. 1, the housing 40 is provided with third gas inlet 42 and adjusting hole 44. The bracket 10 is disposed within the housing 40, and the first gas inlet 12 and the third gas inlet 44 are set in a one-to-one correspondence. That is, the projection of the first gas inlet 12 on the housing 40 is overlapped with the third gas inlet partially or totally. The gas adjusting belt 20 is disposed between the bracket 10 and the housing 40. The gas adjusting toggle 26 protrudes from the adjusting hole 44, so that the user can change the gas intake area of the battery device 100 by dialing the gas adjusting toggle 26.

From this, the present disclosure also provides a gas adjusting assembly, the gas adjusting assembly comprises the bracket 10 and the gas adjusting belt 20 as described above, and the gas adjusting assembly may further include a housing 40. The bracket 10 and the housing 40 may also be components of the atomizer 200, and there is no restriction in this embodiment that the bracket 10 and enclosure 40 are components belonging to the battery device 100 or the atomizer 200.

Different from the prior art, the present disclosure discloses a gas adjusting assembly, a battery device and an electronic atomization equipment. By arranging a bracket and a gas adjusting belt, the bracket is provided with at least one first gas inlet, the gas adjusting belt comprises a flexible belt body and at least one second gas inlet provided on the flexible belt body, and two ends of the flexible belt body are connected to each other and the flexible belt body surrounds a periphery of the bracket. Since the flexible belt body of the gas adjusting belt is foldable, relatively speaking, an installation of the gas adjusting belt has no specific requirements for the shape and structure of the bracket, just surround the bracket by the flexible belt body and connect the two ends of the flexible belt body. By adjusting the gas adjusting belt along a circumferential direction of the bracket, a size of an overlapping area between the second gas inlet and the first gas inlet is adjusted, thereby adjusting the gas intake area of the gas adjusting assembly to obtain different suction feelings. Therefore, the gas adjusting assembly provided in the present disclosure has no specific requirements on the shape and structure of the bracket, and the gas adjusting belt is easy to install.

The above description are only embodiments of the present disclosure, and do not limit the scope of the present disclosure. Any equivalent structure or equivalent process transformation made by using the contents of the description and drawings of the present disclosure, or directly or indirectly used in other related technical fields, are similarly included in the scope of patent protection of the present disclosure.

What is claimed is:

1. A gas adjusting assembly, comprising:
   a bracket, provided with a first gas inlet; and
   a gas adjusting belt, comprising:
      a flexible belt body, surrounding a periphery of the bracket, wherein a first surface of the flexible belt body is provided with a plurality of protrusions, each of the plurality of protrusions comprises a surface away from the flexible belt body, and the surface of each of the plurality of protrusions abuts against a peripheral wall of the bracket; and
      a second gas inlet, disposed through the flexible belt body, the second gas inlet and the first gas inlet being set in a one-to-one correspondence; the flexible belt body being configured to slide relative to the bracket; and the peripheral wall of the bracket is a rectangular peripheral wall, and the flexible belt body surrounds the rectangular peripheral wall.

2. The gas adjusting assembly of claim 1, wherein the flexible belt body is configured to slide relative to the bracket along a circumferential direction of the bracket.

3. The gas adjusting assembly of claim 1, wherein the bracket is further provided with a limiting groove, the gas adjusting belt further comprises a limiting column connected to the flexible belt body, the limiting column is received in the limiting groove, and the limiting groove limits the limiting column.

4. The gas adjusting assembly of claim 3, wherein when the limiting column is located at one end of the limiting groove, the second gas inlet totally overlaps the first gas inlet; when the limiting column is located at the other end of the limiting groove, the second gas inlet is totally misaligned with the first gas inlet.

5. The gas adjusting assembly of claim 3, wherein the gas adjusting assembly further comprises a gas adjusting toggle, the gas adjusting toggle is disposed on a side of the flexible belt body, and is configured to drive the flexible belt body to slide relative to the bracket.

6. The gas adjusting assembly of claim 5, wherein the flexible belt body is further provided with a connecting hole, the connecting hole extends into the limiting column, and an end of the gas adjusting toggle is disposed within a part of the connecting hole defined by the limiting column.

7. The gas adjusting assembly of claim 5, wherein the gas adjusting assembly further comprises a housing, the housing is provided with a third gas inlet and an adjusting hole, the bracket is disposed within the housing, the first gas inlet and the third gas inlet are set in one-to-one correspondence, the gas adjusting belt is disposed between the bracket and the housing, and the gas adjusting toggle protrudes from the adjusting hole.

8. The gas adjusting assembly of claim 1, wherein a peripheral wall of the bracket is provided with an annular groove, the gas adjusting belt is disposed within the annular groove, and the first gas inlet is disposed on a bottom wall of the annular groove.

9. The gas adjusting assembly of claim 1, wherein each of two long sides of the first surface of the flexible belt body is provided with a row of protrusions; and each row of protrusions comprises some of the plurality of protrusions.

10. The gas adjusting assembly of claim 9, wherein the first surface of the flexible belt body is further provided with a plurality of grooves, each of the grooves extends along a width direction of the flexible belt body, and each end of each groove is disposed between two adjacent protrusions of the same row of protrusions.

11. The gas adjusting assembly of claim 1, wherein the flexible belt body is provided with a plurality of grooves, and each of the grooves extends along a width direction of the flexible belt body.

12. The gas adjusting assembly of claim 1, wherein two ends of the flexible belt body are connected to each other, one end is provided with a securing tooth, the other end of the flexible belt body is provided with a securing mouth, and the securing tooth is connected to the securing mouth.

13. The gas adjusting assembly of claim 1, wherein the surface of each of the plurality of protrusions that abuts against the peripheral wall of the bracket is a circular surface.

14. The gas adjusting assembly of claim 9, wherein the first surface of the flexible belt body is further provided with a plurality of grooves, each of the plurality of grooves extends along a width direction of the flexible belt body, and each of the plurality of grooves is disposed between one protrusion of one row of protrusions and one corresponding protrusion of the other row of protrusions along the width direction of the flexible belt body.

15. The gas adjusting assembly of claim 1, wherein the first surface is close to the peripheral wall of the bracket.

* * * * *